(12) United States Patent
Minekawa et al.

(10) Patent No.: US 10,624,712 B2
(45) Date of Patent: Apr. 21, 2020

(54) SENSITIVITY MEASURING DEVICE AND INSPECTION DEVICE

(71) Applicant: Hitachi High-Technologies Corporation, Minato-ku, Tokyo (JP)

(72) Inventors: Hideaki Minekawa, Tokyo (JP); Muneo Maeshima, Tokyo (JP); Akira Masuya, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 217 days.

(21) Appl. No.: 15/568,093

(22) PCT Filed: Mar. 28, 2016

(86) PCT No.: PCT/JP2016/059977
§ 371 (c)(1),
(2) Date: Oct. 20, 2017

(87) PCT Pub. No.: WO2016/170930
PCT Pub. Date: Oct. 27, 2016

(65) Prior Publication Data
US 2018/0079996 A1 Mar. 22, 2018

(30) Foreign Application Priority Data
Apr. 23, 2015 (JP) .................................. 2015-088772

(51) Int. Cl.
*A61B 90/20* (2016.01)
*G01N 21/01* (2006.01)
(Continued)

(52) U.S. Cl.
CPC ............. *A61B 90/20* (2016.02); *C12M 41/12* (2013.01); *C12M 41/36* (2013.01); *G01N 21/01* (2013.01); *H04N 5/00* (2013.01)

(58) Field of Classification Search
CPC ....... A61B 90/20; C12M 41/36; C12M 41/12; G01N 21/02; H04N 5/00
See application file for complete search history.

(56) References Cited

U.S. PATENT DOCUMENTS 8,179,597 B2 5/2012 Namba et al.
9,109,194 B2 8/2015 Honda et al.
(Continued)

FOREIGN PATENT DOCUMENTS

EP 1 988 750 A1 11/2008
JP 2009-93126 A 4/2009
(Continued)

OTHER PUBLICATIONS

International Search Report (PCT/ISA/210) issued in PCT Application No. PCT/JP2016/059977 dated Jun. 7, 2016 with English translation (Three (3) pages).
(Continued)

*Primary Examiner* — Michael L Hobbs
(74) *Attorney, Agent, or Firm* — Crowell & Moring LLP

(57) ABSTRACT

This sensitivity measuring device is provided with: a stage for placing a sample container; a temperature adjustment device that is provided with an upper heating body and a lower heating body, which are disposed above and below the sample container; and an image pickup device for picking up an image of the sample container, said image pickup device being provided with a lighting apparatus and an image pickup apparatus. Each of the upper heating body and the lower heating body has a structure wherein the temperature of a first region, a peripheral portion, is higher than the temperature of a second region including a center portion.

12 Claims, 6 Drawing Sheets

(51) Int. Cl.
 *C12M 1/34* (2006.01)
 *H04N 5/00* (2011.01)

(56) References Cited

U.S. PATENT DOCUMENTS

| | | | | |
|---|---|---|---|---|
| 2002/0012611 | A1* | 1/2002 | Stylli | B01J 19/00 422/65 |
| 2003/0231791 | A1* | 12/2003 | Torre-Bueno | G01N 21/6428 382/133 |
| 2006/0121602 | A1* | 6/2006 | Hoshizaki | G01N 21/645 435/288.7 |
| 2009/0186404 | A1* | 7/2009 | Kim | B01L 3/5027 435/303.1 |
| 2012/0034596 | A1 | 2/2012 | Seidl et al. | |

FOREIGN PATENT DOCUMENTS

| | | |
|---|---|---|
| JP | 2009-201509 A | 9/2009 |
| JP | 2010-91738 A | 4/2010 |
| JP | 2011-103786 A | 6/2011 |
| JP | 5307539 B2 | 10/2013 |
| WO | WO 2007/092571 A2 | 8/2007 |

OTHER PUBLICATIONS

Japanese-language Written Opinion (PCT/ISA/237) issued in PCT Application No. PCT/JP2016/059977 dated Jun. 7, 2016 (Three (3) pages).

Extended European Search Report issued in counterpart European Application No. 16782952.2 dated Oct. 10, 2018 (eight (8) pages).

* cited by examiner

SENSITIVITY MEASURING DEVICE AND INSPECTION DEVICE

TECHNICAL FIELD

The present invention relates to a sensitivity measuring device and an inspection device including the same.

BACKGROUND ART

Antibiotic susceptibility testing of bacteria is performed by culturing a sample container containing bacteria and an antibacterial agent under an environment adjusted to a temperature suitable for proliferation of bacteria and by measuring the degree of proliferation using absorbency, turbidity, and the like. Currently, an inspection is performed on the proliferation of bacteria by turbidity measurement, visual observation, or optical measurement of absorbency after overnight culture.

To determine the degree of proliferation of bacteria, by performing the culture for a long time at a temperature suitable for the proliferation of bacteria, the degree of proliferation of bacteria is determined by sufficiently differentiating the state of proliferation. In United States Clinical and Laboratory Standards Institute (CLSI), culture conditions at this time are defined as 35° C.±2° C. Here, in the susceptibility inspection, since the determination is made based on whether or not the variation in proliferation due to the temperature difference of a culture solution exceeds the prescribed turbidity after culturing for a long time, the temperature variation of about ±2° C. is not matter.

The long culture time of whole day and night and the subsequent inspection process will result in delayed dosing and a heavy burden on the patient. Therefore, shortening of the inspection is desired for rapid treatment. In order to determine the proliferation of bacteria in a short time, it is important to manage the culture solution of each well in the sample container at a uniform temperature, and set the same culture conditions among the wells as much as possible.

Usually, in a sample container having a plurality of wells, the culture is performed using an incubator (constant temperature bath). However, in the conventional device, it is not possible to perform an optical measurement by disposing an image pickup apparatus inside the incubator. Further, there is a device that heats a sample container with an incubator and conveys the sample container to a measuring unit at the time of turbidity measurement (PTL 1). However, in such a device, there is a problem that the temperature of the sample container decreases while an image is picked up using the image pickup apparatus.

Since the turbidity measurement can be performed in a relatively short time, the temperature drop during measurement can be ignored. However, it takes a long time to perform the image pickup with the image pickup apparatus, and the temperature of the sample container decreases during image pickup of all the wells, which causes variations in subsequent proliferation. For this reason, it is difficult to obtain an accurate determination result.

Meanwhile, there is a device that heats the sample container using a heating device (a heat plate) directly under the measuring device (PTL 2). In the case of this device, it is difficult to equalize the temperature of the culture solution in each well of the sample container. Generally, the reason is that heat is easy to escape at the end portion of the heat plate, and the temperature drops. Even in this case, variations will occur in the subsequent amount of the proliferation of bacteria, making it difficult to obtain an accurate determination result.

CITATION LIST

Patent Literature

PTL 1: JP 2011-103786 A
PTL 2: JP 5307539 B2

SUMMARY OF INVENTION

Technical Problem

In order to determine the result of the antibiotic susceptibility testing from the result of the bacterial culture in a short time, it is necessary to make the culture condition in the sample container more uniform as compared with the case of the conventional susceptibility testing which is performed over a whole day and night. In particular, the temperature condition has a large influence on the cell culture, and it is necessary to reduce variations in temperature in the sample container.

The present invention provides a technique capable of uniformly maintaining the temperature condition inside the sample container.

Solution to Problem

For example, in order to solve the above problem, the configuration described in the claims is adopted. The present application includes some solutions and as one example, there is provided a sensitivity measuring device including: a stage on which a sample container is mounted; a temperature adjustment device including an upper heating body and a lower heating body disposed above and below the sample container; an image pickup device for picking up an image of the sample container, the image pickup device including a lighting apparatus and an image pickup apparatus, wherein each of the upper heating body and the lower heating body has a structure in which a temperature of a first region which is a peripheral portion is higher than a temperature of a second region including a center portion.

Advantageous Effects of Invention

According to the present invention, it is possible to uniformly maintain the temperature condition in the sample container in the sensitivity measuring device. Further features relating to the present invention will become apparent from the description of this specification and the accompanying drawings. In addition, the problems, configurations and effects other than those described above will be clarified by the description of the following examples.

DESCRIPTION OF EMBODIMENTS

Hereinafter, examples of the present invention will be described with reference to the accompanying drawings. Although the accompanying drawings illustrate specific examples according to the principle of the present invention, the drawings are for understanding of the present invention and are never used to interpret the present invention in a limited way.

In the following description, an XYZ orthogonal coordinate system is set, and a positional relation of each member will be described with reference to this XYZ orthogonal coordinate system. A predetermined direction in a horizontal plane is defined as an X-axis direction, a direction orthogonal to the X-axis direction in the horizontal plane is defined as a Y-axis direction, a direction orthogonal to each of the X-axis direction and the Y-axis direction (that is, a vertical direction) is defined as a Z-axis direction.

The following examples relate to an inspection device which performs the heating culture of bacteria in the sample container and determines the antibiotic susceptibility. The inspection device includes a bacteria susceptibility measuring device. The bacteria susceptibility measuring device measures a proliferation amount of bacteria at predetermined time intervals, using an optical measuring device. The inspection device is a device that accumulates measurement data obtained by the optical measuring device and determines the antibiotic susceptibility by analyzing a change in proliferation amount from the measured data.

FIRST EXAMPLE

Figure 1:
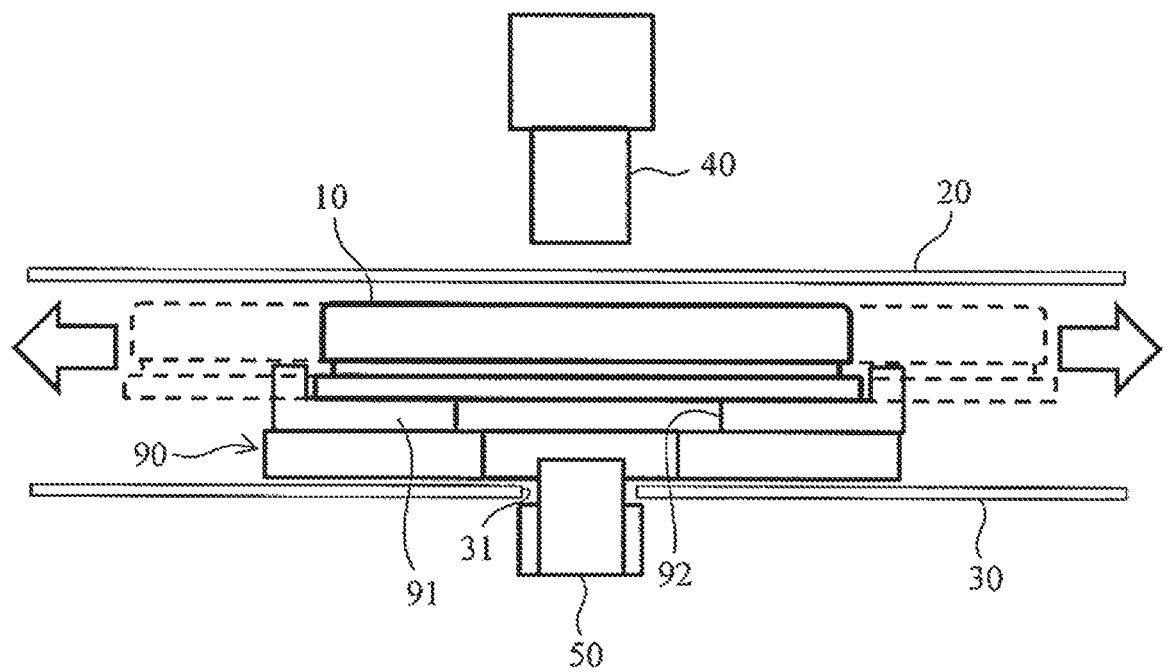
FIG. 1 is a cross-sectional view illustrating a configuration of a bacteria susceptibility measuring device according to a first example.

FIG. 1 is a cross-sectional view illustrating a configuration of a bacteria susceptibility measuring device according to the first example. The bacteria susceptibility measuring device is a device which optically measures each well of a sample container 10 in order to inspect the antibiotic susceptibility of bacteria. As an example, the sample container 10 has ninety-six wells.

The bacteria susceptibility measuring device includes an XY stage 90 for mounting the sample container 10, a temperature adjustment device for controlling the temperature of the sample container 10 to promote the culture of bacteria, and an image pickup apparatus 50 for performing the optical measurement of bacteria after culture. The XY stage 90 has a mounting table 91 on which the sample container 10 having a plurality of wells is mounted. The XY stage 90 is configured to be capable of moving the sample container 10 in the X-axis direction and the Y-axis direction.

The temperature adjustment device is a device for uniformly maintaining the temperature of the plurality of wells of the sample container 10. The temperature adjustment device includes an upper heating body 20 and a lower heating body 30. In this example, the upper heating body 20 and the lower heating body 30 are heaters. It should be noted that the upper heating body 20 and the lower heating body 30 are supported at positions sandwiching the XY stage 90 therebetween, using a support mechanism (not illustrated). The sample container 10 is disposed between the upper heating body 20 and the lower heating body 30 so as not to come into contact with the upper heating body 20 and the lower heating body 30 by the XY stage 90.

Figure 2:
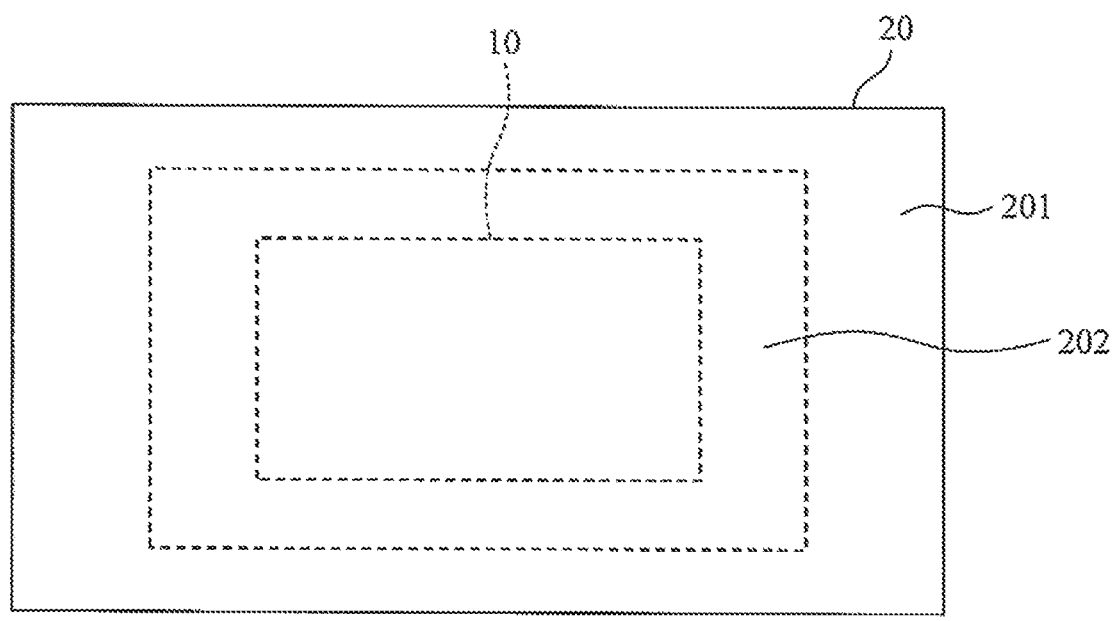
FIG. 2 is a plan view of an upper heating body in the bacteria susceptibility measuring device according to the first example.
Figure 3:
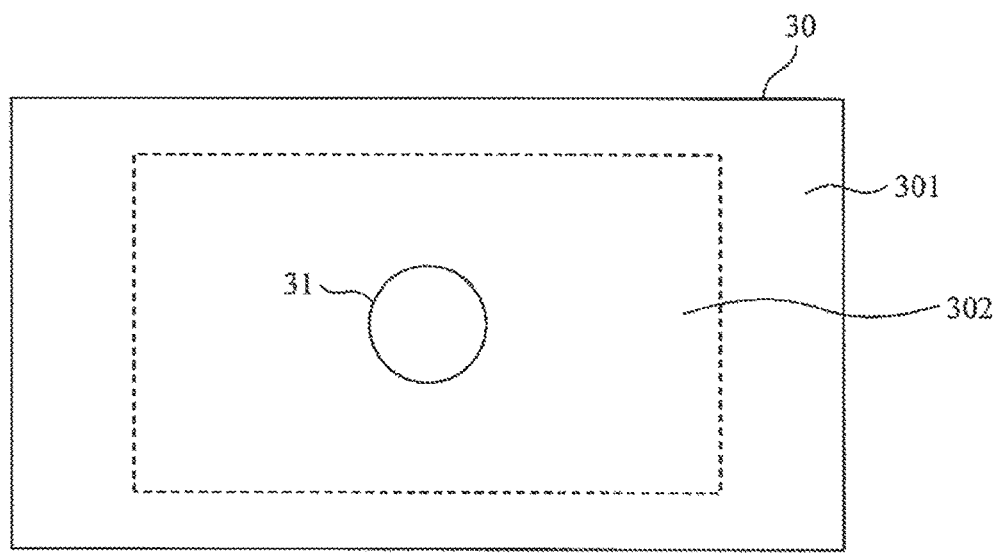
FIG. 3 is a plan view of a lower heating body in the bacteria susceptibility measuring device according to the first example.

FIG. 2 is a plan view of the upper heating body 20, and FIG. 3 is a plan view of the lower heating body 30. As the feature of the present invention, the upper heating body 20 has a structure in which the temperature of a first region 201, which is a peripheral portion of the upper heating body 20, is higher than the temperature of a second region 202 including a center portion. Similarly, the lower heating body 30 has a structure in which the temperature of a first region 301, which is a peripheral portion of the lower heating body 30, is higher than the temperature of a second region 302 including a center portion. Heat is easy to escape from the end portions of the upper heating body 20 and the lower heating body 30, and the temperature easily decreases. By raising the temperatures of the first region 201 of the upper heating body 20 and the first region 301 of the lower heating body 30 from which heat easily escapes, it is possible to uniformly keep the temperature of the plurality of wells of the sample container 10 held inside the first region 201 and the first region 301.

In this example, the upper heating body 20 is a glass heater. The glass heater has a structure in which a transparent heat generating body is sandwiched between the two glasses. As an example, a glass heater is made by depositing a transparent heat generating body on the glass. As described above, in order to provide a temperature difference between the first region 201 and the second region 202, the transparent heat generating bodies may be closely disposed in the first region 201 from which the temperature is easy to escape, and the transparent heat generating bodies may be sparsely disposed in the second region 202. As an example, it is assumed that the transparent heat generating bodies are linearly deposited on the glass. In this case, the interval between the adjacent linear transparent heat generating bodies in the first region 201 is smaller than the interval between the adjacent linear transparent heat generating bodies in the second region 202. According to this configuration, the amount of heat generation in the first region 201 is larger than the amount of heat generation in the second region 202. This makes it possible to reduce variations in temperature between the first region 201 and the second region 202 and to uniformly keep the temperatures of the plurality of wells of the sample container 10 held inside the first region 201 and the second region 202.

Further, in the upper heating body 20, the amount of heat generation in the first region 201 may be larger than the amount of heat generation in the second region 202, and the invention is not limited to the above configuration. For example, it is assumed that the transparent heat generating bodies are deposited on the glass in the form of a film. In this case, the amount of heat generation may be changed by changing the thickness of the film-like transparent heat generating body in the second region 202 with respect to the thickness of the film-like transparent heat generating body in the first region 201. As an example, the thickness of the film-like transparent heat generating body in the first region 201 may be larger than the thickness of the film-like transparent heat generating body in the second region 202. According to this configuration, the amount of heat generation in the first region 201 is larger than the amount of heat generation in the second region 202. This makes it possible to reduce variations in temperature between the first region 201 and the second region 202 and to uniformly keep the temperatures of the plurality of wells of the sample container 10 held inside the first region 201 and the second region 202.

In this example, the lower heating body 30 is a heater made of an opaque material. As an example, a heater is made by mounting a nichrome wire on a metal plate. As in the upper heating body 20, the lower heating body 30 has a structure in which the amount of heat generation in the first region 301 is larger than the amount of heat generation in the second region 302. As an example, in order to provide a temperature difference between the first region 301 and the second region 302, the heat generating bodies may be densely disposed in the first region 301 from which temperature is easy to escape, and the heat generating bodies may be sparsely disposed in the second region 302. For example, the interval between adjacent nichrome wires (linear heat generating bodies) in the first region 301 is smaller than the interval between adjacent nichrome wires in the second region 302. This makes it possible to reduce variations in temperature between the first region 301 and the second region 302 and to uniformly keep the temperatures of the plurality of wells of the sample container 10 held inside the first region 301 and the second region 302.

Further, the upper heating body 20 and the lower heating body 30 are not limited to the above-described configuration. The upper heating body 20 and the lower heating body 30 may adopt other configurations other than those described above as long as the amounts of heat generation in the first regions 201 and 301 are larger than the amounts of heat generation in the second regions 202 and 302.

Further, the upper heating body 20 and the lower heating body 30 have a sufficiently larger size than the sample container 10 so that variations in amount of heat generation do not affect the sample container 10. For example, in the plan view, the sizes of the upper heating body 20 and the lower heating body 30 have such a size as to cover the sample container 10. FIG. 2 illustrates an example of the relation between the sizes of the upper heating body 20 and the sample container 10.

As illustrated in FIG. 1, the sample container 10 is moved in the X-axis direction and the Y-axis direction (within the range described by the dotted line) by the XY stage 90. Therefore, in the plan view, the planar sizes of the upper heating body 20 and the lower heating body 30 are larger than the movement range of the sample container 10 in the X-axis direction and the Y-axis direction. As an example, the planar sizes of the upper heating body 20 and the lower heating body 30 are four times or more the planar size of the sample container 10.

The image pickup device includes a lighting apparatus 40 and an image pickup apparatus 50. As illustrated in FIG. 1, the lighting apparatus 40 is disposed above the upper heating body 20. Further, the image pickup apparatus 50 is disposed below the lower heating body 30. In this example, since the upper heating body 20 is a glass heater, the sample container 10 can be irradiated with light even if the lighting apparatus 40 is disposed above the upper heating body 20. Further, in the case of the glass heater, there is no need to provide holes for the lighting apparatus 40, and there is an advantage that the temperature condition of the well of the sample container 10 can be easily maintained more uniformly.

On the other hand, since the lower heating body 30 is a heater made of an opaque material, the lower heating body 30 is provided with a hole 31 for the image pickup apparatus 50. A hole 92 for the image pickup apparatus 50 is provided on the mounting table 91 of the XY stage 90. The lens of the image pickup apparatus 50 is inserted into the hole 31 of the lower heating body 30. The image pickup apparatus 50 is capable of picking up the image of the sample container 10 via the hole 31 and the hole 92. As a result, while keeping the temperature of the sample container 10 by the temperature adjustment device, it is possible to pick up an image of the sample container 10, using the image pickup apparatus 50. When the hole 31 for the image pickup apparatus 50 is provided in the lower heating body 30, the lower heating body 30 is in a fixed position without moving. Only the sample container 10 is moved by the XY stage 90.

Figure 4:
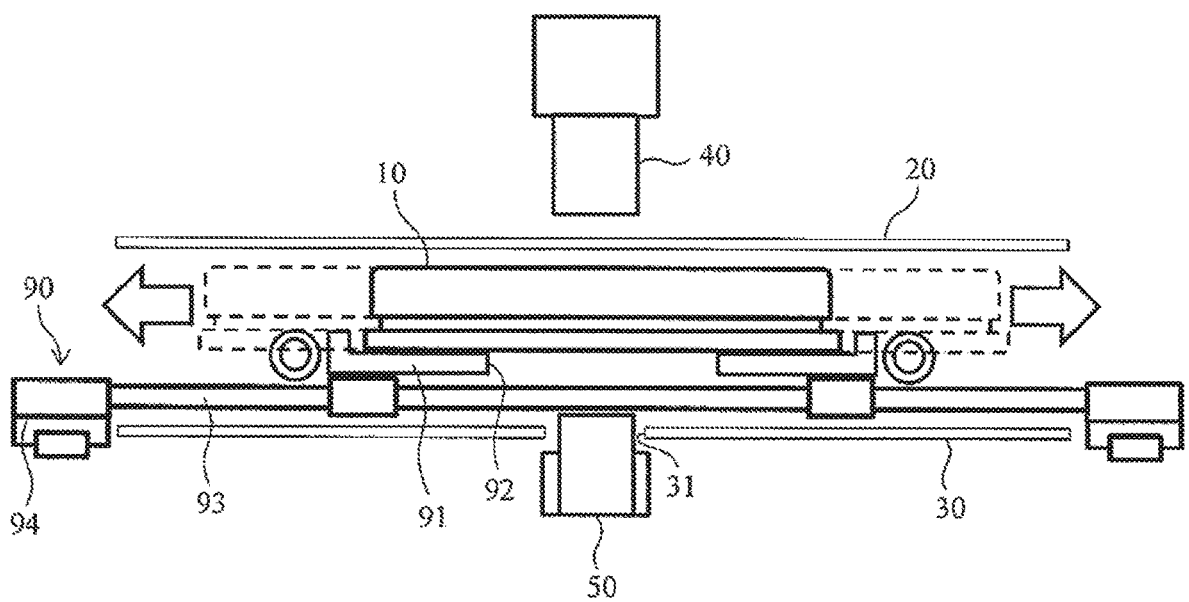
FIG. 4 is a cross-sectional view illustrating another example of an XY stage.

FIG. 4 is a cross-sectional view illustrating another example of the XY stage in the bacteria susceptibility measuring device according to the first example. The XY stage 90 may include a rail 93 for moving the mounting table 91 in the X-axis direction and the Y-axis direction, and a driving mechanism 94 for driving the movement of the mounting table 91. In this manner, the driving mechanism 94 for driving the movement of the sample container 10 may be disposed outside the upper heating body 20 and the lower heating body 30. The configuration of the XY stage is not limited to the two configurations described above and can be appropriately changed.

As described above, various configurations can be adopted for the XY stage 90, and the distance between the upper heating body 20 and the sample container 10, and the distance between the lower heating body 30 and the sample container 10 change by the configuration of the XY stage 90, and the like. Considering them, the temperature of the first region 201 of the upper heating body 20, the temperature of the second region 202 of the upper heating body 20, the temperature of the first region 301 of the lower heating body 30, and the temperature of the second region 302 of the lower heating body 30 may be appropriately set, respectively.

SECOND EXAMPLE

Figure 5:
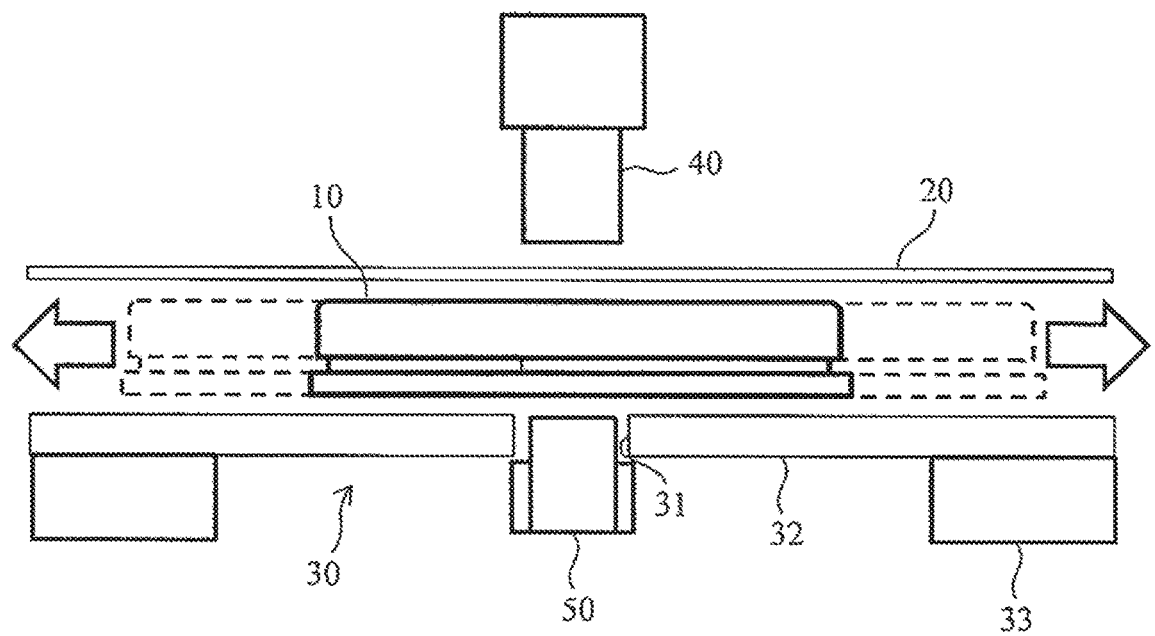
FIG. 5 is a cross-sectional view illustrating a configuration of a bacteria susceptibility measuring device according to a second example.

FIG. 5 is a cross-sectional view illustrating a configuration of a bacteria susceptibility measuring device according to a second example. In FIG. 5, in order to briefly describe the configuration of the invention, the XY stage 90 is omitted.

In this example, the lower heating body 30 includes a plate 32 made of a material having thermal conductivity, and a heat generating body 33. As the plate 32, a metal plate having good thermal conductivity may be adopted. The heat generating body 33 is disposed, for example, in the first region 301 of the lower heating body 30. By disposing the heat generating body 33 in the first region 301 which is the peripheral portion of the lower heating body 30, the temperature of the first region 301 from which temperature is easy to escape can be set to be higher than that of the second region 302. This makes it possible to reduce variations in temperature between the first region 301 and the second region 302 and to uniformly keep the temperatures of the plurality of wells of the sample container 10 held inside the first region 301 and the second region 302. Further, according to the present example, the temperature adjustment device can be configured with a simple structure in which the heat generating body itself is not disposed directly below the sample container 10.

The above configuration can also be applied to the upper heating body 20. The upper heating body 20 may include a plate made of a material having good thermal conductivity, and a heat generating body. In this case, it is necessary to provide a hole for the lighting apparatus 40 in the upper heating body 20.

THIRD EXAMPLE

Figure 6:
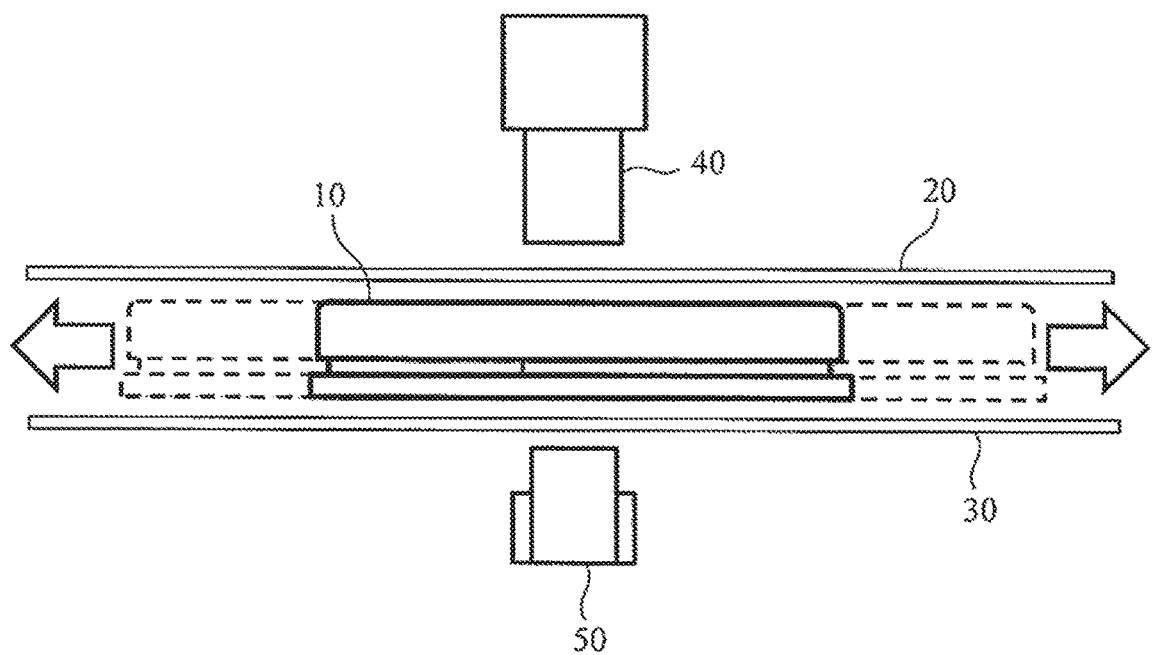
FIG. 6 is a cross-sectional view illustrating a configuration of a bacteria susceptibility measuring device according to a third example.

FIG. 6 is a cross-sectional view illustrating a configuration of a bacteria susceptibility measuring device according to a third example. In FIG. 6, in order to briefly describe the configuration of the invention, the XY stage 90 is omitted.

The lower heating body 30 may be constituted by the above-mentioned glass heater. The glass heater is made by depositing a transparent heat generating body on the glass. As described above, in order to provide a temperature difference between the first region 301 and the second region 302, the transparent heat generating bodies may be densely disposed in the first region 301 from which temperature is easy to escape, and the transparent heat generating bodies may be sparsely disposed in the second region 302. As an example, when linearly depositing the transparent heat generating bodies on the glass, the interval between the adjacent linear transparent heat generating bodies in the first region 301 is smaller than the interval between the adjacent linear transparent heat generating bodies in the second region 302.

Further, when depositing the transparent heat generating bodies on the glass in the form of a film, the thickness of the film-like transparent heat generating body in the first region 301 may be made larger than the thickness of the film-like transparent heat generating body in the second region 302.

According to the present example, it is possible to pick up an image of the sample container 10 with the image pickup apparatus 50, without providing holes for the image pickup apparatus 50 in the lower heating body 30. Further, by not forming a hole in the lower heating body 30, there is an advantage that it is easy to make the amount of heat generation of the lower heating body 30 more uniform.

FOURTH EXAMPLE

Figure 7:
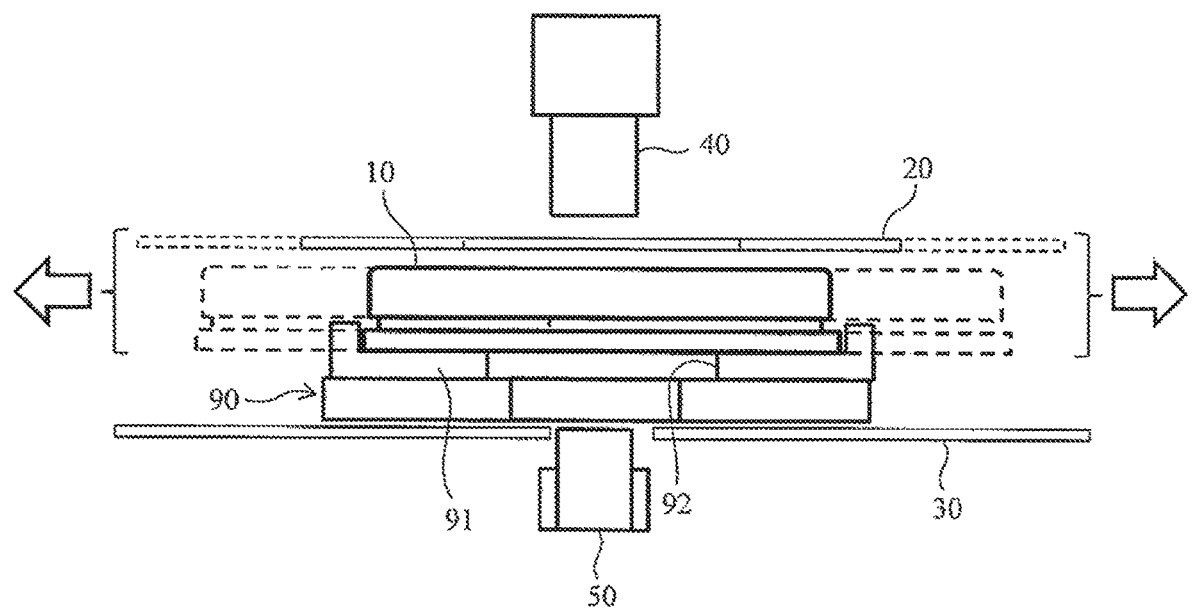
FIG. 7 is a cross-sectional view illustrating a configuration of a bacteria susceptibility measuring device according to a fourth example.

FIG. 7 is a cross-sectional view illustrating a configuration of a bacteria susceptibility measuring device according to a fourth example. In this example, an upper heating body 20 includes the above-described glass heater. Further, the upper heating body 20 is connected to the XY stage 90. Therefore, the upper heating body 20 moves together with the sample container 10 in the X-axis direction and the Y-axis direction (within the range indicated by the dotted line) by the movement of the XY stage 90.

According to this example, since the upper heating body 20 moves in the X-axis direction and the Y-axis direction together with the sample container 10, the planar size of the upper heating body 20 may be the same as the planar size of the sample container 10, or may have a slightly larger size. That is, there is no need to make the planar size of the upper heating body 20 large enough to cover the movement range of the sample container 10, and the planar size of the upper heating body 20 can be designed to be smaller than the above examples. In this example, since the lower heating body 30 is fixed, the planar size of the lower heating body 30 has a larger size than the movement range of the sample container 10 in the X-axis direction and the Y-axis direction.

FIFTH EXAMPLE

Figure 8:
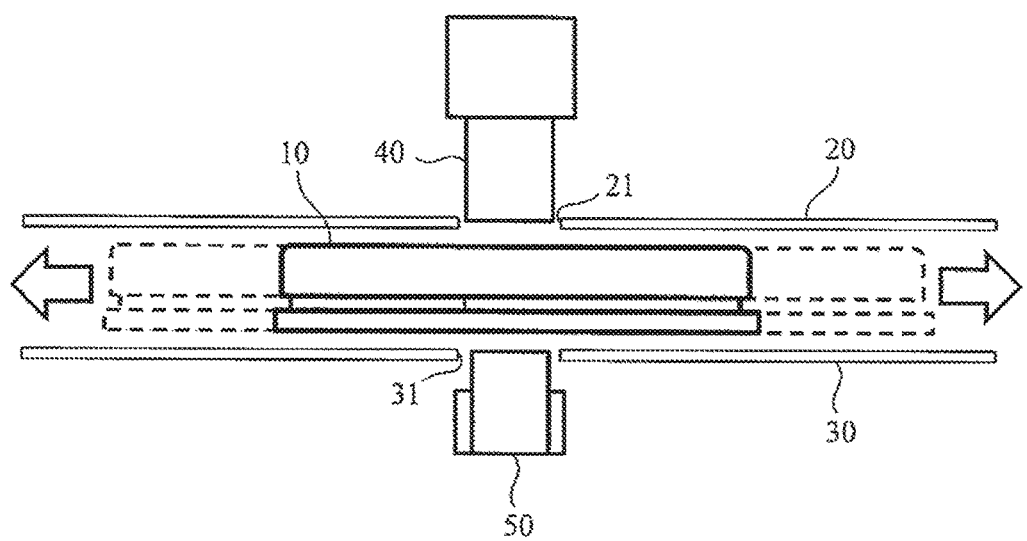
FIG. 8 is a cross-sectional view illustrating a configuration of a bacteria susceptibility measuring device according to a fifth example.

FIG. 8 is a cross-sectional view illustrating a configuration of a bacteria susceptibility measuring device according to a fifth example. In FIG. 8, in order to briefly describe the configuration of the invention, the XY stage 90 is omitted.

In this example, the upper heating body 20 is a heater made of an opaque material. As an example, the heater is formed by mounting a nichrome wire on a metal plate. The upper heating body 20 has a structure in which the amount of heat generation in the first region 201 is larger than the amount of heat generation in the second region 202. As an example, in order to provide a temperature difference between the first region 201 and the second region 202, the heat generating bodies may be densely disposed in the first region 201 from which temperature is easy to escape, and the heat generating bodies maybe sparsely disposed in the second region 202. For example, the interval between the adjacent nichrome wires in the first region 201 is smaller than the interval between the adjacent nichrome wires in the second region 202. This makes it possible to reduce variations in temperature between the first region 201 and the second region 202 and to uniformly keep the temperatures of the plurality of wells of the sample container 10 held inside the first region 201 and the second region 202.

Further, in this example, since the upper heating body 20 is made of an opaque material, the upper heating body 20 has a hole 21 for the lighting apparatus 40. The lighting apparatus 40 can light the sample container 10 via the hole 21. As in the above-described example, the sizes of the upper heating body 20 and the lower heating body 30 in a plan view have the size that is larger than the movement range of the sample container 10 in the X-axis direction and the Y-axis direction.

SIXTH EXAMPLE

Figure 9:
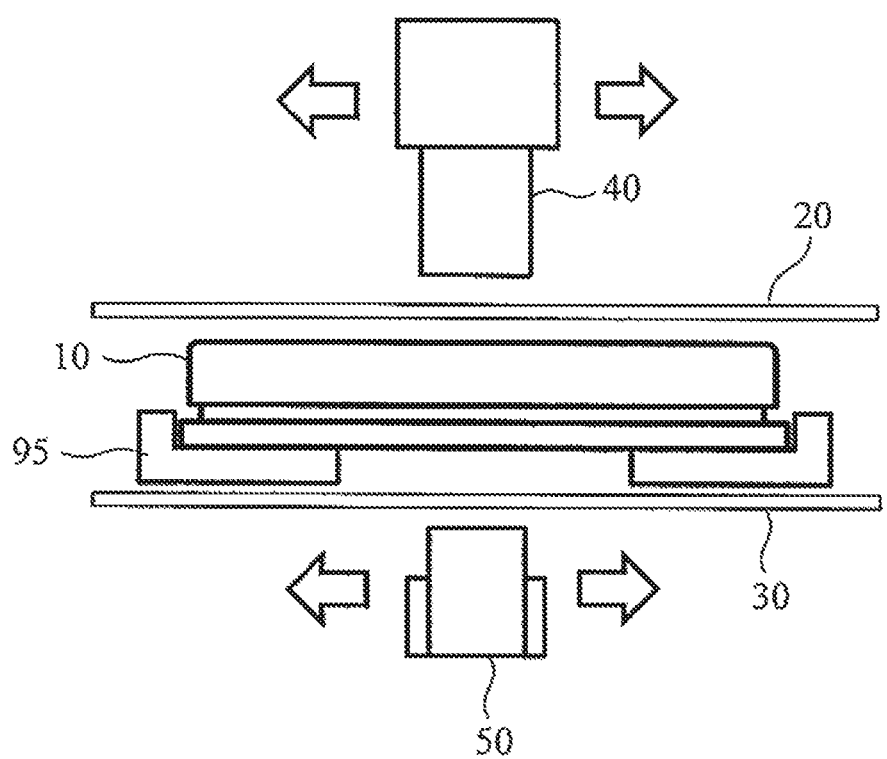
FIG. 9 is a cross-sectional view illustrating a configuration of a bacteria susceptibility measuring device according to a sixth example.

FIG. 9 is a cross-sectional view illustrating a configuration of a bacteria susceptibility measuring device according to a sixth example. In the above examples, the configuration in which holes are provided in at least one of the upper heating body 20 and the lower heating body 30 has been described. However, in such a configuration, it is necessary to make the upper heating body 20 and the lower heating body 30 sufficiently large with respect to the sample container so that the temperature decrease at the end portions thereof does not affect the proliferation amount of the bacteria in the sample container 10. The measuring device itself also increases in size, accordingly. To solve this problem, a configuration may be adopted in which the positions of the upper heating body 20 and the lower heating body 30 and the position of the sample container 10 are fixed, and the lighting apparatus 40 and the image pickup apparatus 50 are moved.

For example, the sample container 10 is mounted on a stage 95 that does not move in the X-axis direction and the Y-axis direction. Further, the lighting apparatus 40 and the image pickup apparatus 50 are connected to each other and are provided as an integrated optical measuring unit. The lighting apparatus 40 and the image pickup apparatus 50 are supported by an XY stage (not illustrated), respectively. With this XY stage, the lighting apparatus 40 and the image pickup apparatus 50 move together in the X-axis direction and the Y-axis direction. The upper heating body 20 and the lower heating body 30 have the structure of the above-described glass heater. As a result, all the wells in the sample container 10 can be measured by an integrated optical measuring unit.

According to the present example, it is not necessary to set the planar sizes of both the upper heating body 20 and the lower heating body 30 to such a size as to cover the movement range of the sample container 10. The planar sizes of both the upper heating body 20 and the lower heating body 30 can be designed to be smaller than those in the above examples. Therefore, it is possible to reduce the size of the bacteria susceptibility measuring device.

SEVENTH EXAMPLE

Figure 10:
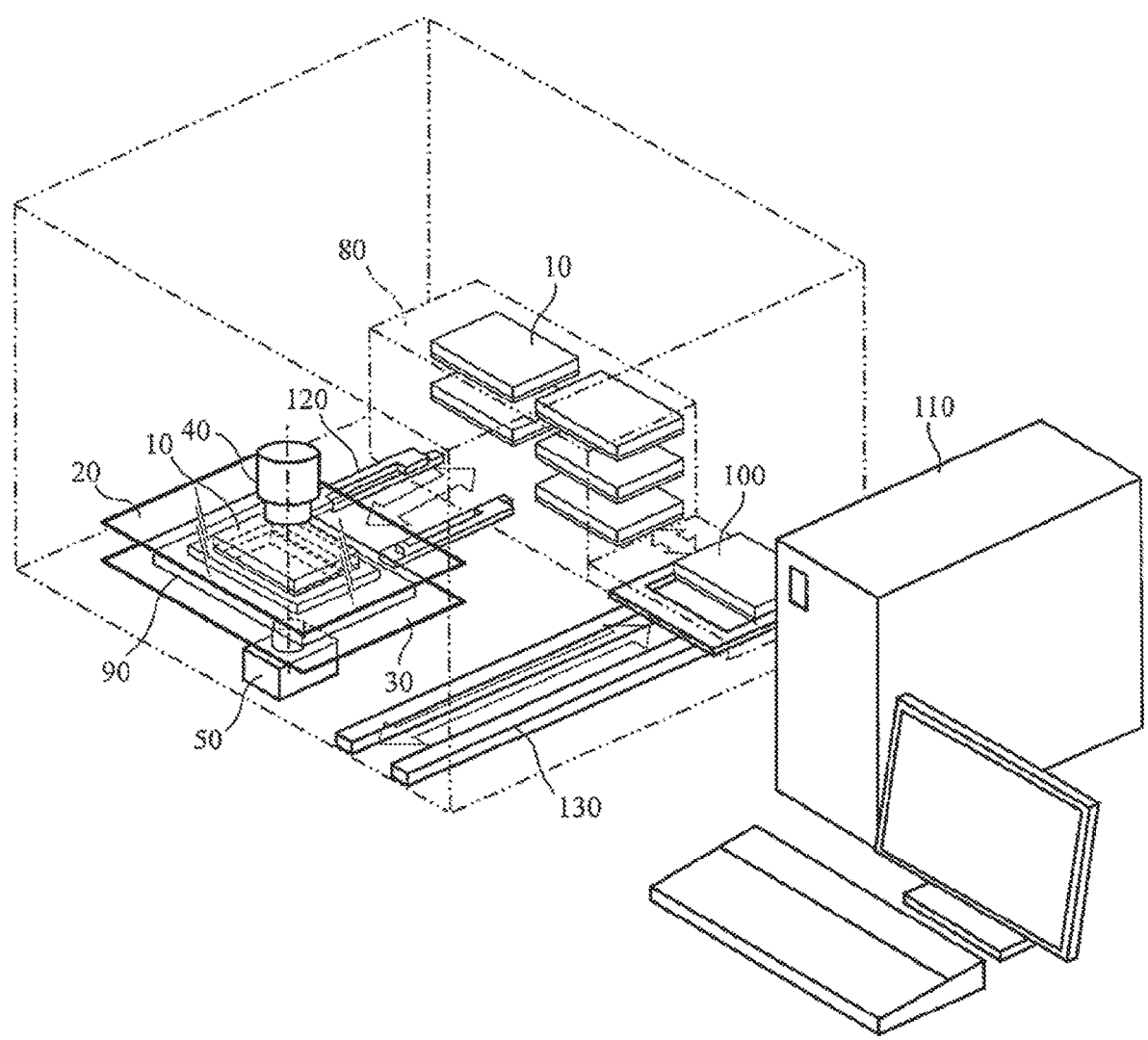
FIG. 10 is an example of an inspection device including a bacteria susceptibility measuring device.

FIG. 10 illustrates an example of an inspection device including the bacteria susceptibility measuring device of the first to sixth examples. The inspection device includes a stack unit 80. The stack unit 80 is a thermostatic tank capable of simultaneously culturing a plurality of sample containers 10. The stack unit 80 has a mechanism capable of moving the storage position of the sample container 10 therein, can freely select the sample container 10 to be measured, and can supply the sample container 10 to a conveying unit to be described below.

The inspection device includes a feed chamber 100 that supplies the sample container 10 to the stack unit 80 and is capable of discharging the sample container 10 from the stack unit 80. The sample container 10 is supplied to the feed chamber 100, using a first conveying unit 130. In the feed chamber 100, it is possible to heat the sample container 10, and after heating to the temperature of the sample container 10 in the stack unit 80, the sample container 10 is supplied to the stack unit 80. Accordingly, the sample container 10 can be taken in and out, without lowering the temperature of the measuring chamber and the stack unit 80. A second conveying unit which conveys the sample container 10 is provided between the feed chamber 100 and the stack unit 80.

A third conveying unit 120 is provided between the XY stage 90 and the stack unit 80. It is possible to convey only the sample container 10 to be measured from the stack unit 80 to the XY stage 90, using the third conveying unit 120. Further, the third conveying unit 120 again conveys the sample container 10, in which the measurement has been completed, to the stack unit 80.

The inspection device includes a control personal computer 110. The control personal computer 110 can manage the culture starting time. Further, the control personal computer 110 can control the entire inspection device. The control personal computer 110 can control the conveyance of the sample container 10, the start of measurement, and the like, without stopping the measurement sequence, and it is possible to perform the inspection at all times.

The above-mentioned bacteria susceptibility measuring device includes a temperature adjustment device for adjusting the temperature of the sample container 10 to promote culture of bacteria, and an image pickup device which performs the optical measurement of bacteria after culture. Further, the bacteria susceptibility measuring device includes an XY stage capable of moving the sample container 10 or the image pickup device in the X-axis direction and the Y-axis direction in order to measure a plurality of wells in the sample container 10. As a feature of the above example, the temperature adjustment device includes the upper heating body 20 and the lower heating body 30. Each of the upper heating body 20 and the lower heating body 30 has a structure in which there is a difference in amount of heat generation between the peripheral portion and the center portion or there is a difference in temperature between the peripheral portion and the center portion. As a result, the difference in temperature in the sample container 10 can be made as small as possible, and the culture under the same temperature condition can be performed. In addition, it is possible to pick up an image of the sample container 10 with the image pickup device, while maintaining the same temperature condition.

According to the above configuration, it is possible to measure the proliferation amount of bacteria in the sample container 10 cultured under uniform temperature condition at predetermined time intervals, and to determine the antibiotic susceptibility from the change in the amount thereof. Further, by analyzing the change in the proliferation amount of the bacteria, it is possible to provide an inspection device capable of determining the result of the susceptibility inspection in a short time.

The present invention is not limited to the above-described examples, but includes various modified examples. The above examples have been described in detail in order to explain the present invention in an easy-to-understand manner, and are not necessarily limited to those having all the configurations described. Further, a part of the configuration of an example can be replaced by the configuration of another example. Further, the configuration of another example can be added to the configuration of an example. Further, other configurations can be added, deleted, or replaced with respect to a part of the configuration of each example.

REFERENCE SIGNS LIST 10 sample container
20 upper heating body
21 hole
30 lower heating body
31 hole
32 plate
33 heat generating body
40 lighting apparatus
50 image pickup apparatus
80 stack unit
90 XY stage
91 mounting table
92 hole
93 rail
94 driving mechanism
95 stage
100 feed chamber
110 control personal computer
120 third conveying unit
130 first conveying unit
201 first region of upper heating body
202 second region of upper heating body
301 first region of lower heating body
302 second region of lower heating body

The invention claimed is:

1. A sensitivity measuring device comprising:
a stage on which a sample container is mounted; a temperature adjustment device including an upper heating body and a lower heating body disposed above and below the sample container; and an image pickup device for picking up an image of the sample container, the image pickup device including a lighting apparatus and an image pickup apparatus, wherein each of the upper heating body and the lower heating body has a structure in which a temperature of a first region which is a peripheral portion is higher than a temperature of a second region including a center portion, and within both the upper heating body and the lower heating body, the respective first region completely encloses the corresponding second region therein.

2. The sensitivity measuring device according to claim 1, wherein the upper heating body and the lower heating body have a structure in which an amount of heat generation of the first region is larger than an amount of heat generation of the second region.

3. The sensitivity measuring device according to claim 2, wherein at least one of the upper heating body and the lower heating body includes a linear heat generating body, and includes a structure in which an interval between adjacent linear heat generating bodies in the first region is larger than an interval between adjacent linear heat generating bodies in the second region.

4. The sensitivity measuring device according to claim 2, wherein at least one of the upper heating body and the lower heating body includes a heat generating body, and includes a structure in which the thickness of the heat generating body in the first region is larger than the thickness of the heat generating body in the second region.

5. The sensitivity measuring device according to claim 1, wherein at least one of the upper heating body and the lower heating body is a glass heater.

6. The sensitivity measuring device according to claim 5, wherein the upper heating body is a glass heater, the lighting apparatus is disposed above the upper heating body, the lower heating body has a hole for the image pickup apparatus, and the image pickup apparatus is disposed below the lower heating body.

7. The sensitivity measuring device according to claim 1, wherein the stage is an XY stage which moves the sample container in an X-axis direction and a Y-axis direction, and each of the upper heating body and the lower heating body has a planar size larger than a movement range of the XY stage.

8. The sensitivity measuring device according to claim 1, wherein the upper heating body has a hole for the lighting apparatus, the lighting apparatus is disposed above the upper heating body, the lower heating body has a hole for the image pickup apparatus, and the image pickup apparatus is disposed below the lower heating body.

9. The sensitivity measuring device according to claim 1, wherein at least one of the upper heating body and the lower heating body includes a plate having thermal conductivity, and a heat generating body disposed at a position corresponding to the first region of the plate.

10. The sensitivity measuring device according to claim 1, further comprising:

an XY stage which moves the lighting apparatus and the image pickup apparatus in an X-axis direction and a Y-axis direction, wherein the upper heating body and the lower heating body are glass heaters.

11. An inspection device comprising:

the sensitivity measuring device according to claim 1;

a tank which functions as a constant temperature bath of the sample container, where the temperature of the sample container is raised before entering the tank; and a conveyor which conveys the sample container from the tank to the stage of the sensitivity measuring device.

12. A sensitivity measuring device comprising:

a stage on which a sample container is mounted;

a temperature adjustment device including an upper heating body and a lower heating body disposed above and below the sample container; and an image pickup device for picking up an image of the sample container, the image pickup device including a lighting apparatus and an image pickup apparatus, wherein each of the upper heating body and the lower heating body has a structure in which a temperature of a first region which is a peripheral portion is higher than a temperature of a second region including a center portion, and the stage is an XY stage which moves the sample container in an X-axis direction and a Y-axis direction, the upper heating body is connected to the XY stage, and the lower heating body has a planar size larger than a movement range of the XY stage.

* * * * *